(12) United States Patent
Maekawa et al.

(10) Patent No.: US 7,018,815 B2
(45) Date of Patent: Mar. 28, 2006

(54) METHOD FOR PRODUCING VITAMIN B12 FROM HYDROGEN-METABOLIZING METHANE BACTERIUM

(75) Inventors: Takaaki Maekawa, Ibaraki (JP); Zhen Ya Zhang, Ibaraki (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 11/155,613

(22) Filed: Jun. 20, 2005

(65) Prior Publication Data

US 2005/0227332 A1   Oct. 13, 2005

Related U.S. Application Data

(62) Division of application No. 10/182,624, filed as application No. PCT/JP01/00720 on Feb. 1, 2001, now Pat. No. 6,972,188.

(30) Foreign Application Priority Data

Feb. 1, 2000   (JP) ............................. 2000-024490

(51) Int. Cl.
*C12P 5/02*     (2006.01)
*C12P 19/42*    (2006.01)
*C12P 3/00*     (2006.01)

(52) U.S. Cl. .............. 435/86; 95/55; 96/4; 210/500.26; 427/255.11; 427/255.12

(58) Field of Classification Search ................... 435/86; 514/52; 427/255.11, 255.12; 95/55; 96/4; 210/500.26
See application file for complete search history.

(56) References Cited

U.S. PATENT DOCUMENTS

| | | | |
|---|---|---|---|
| 6,331,236 B1 * | 12/2001 | Mani | 204/525 |
| 6,494,937 B1 * | 12/2002 | Edlund et al. | 96/4 |
| 6,824,593 B1 * | 11/2004 | Edlund et al. | 96/4 |
| 6,854,602 B1 * | 2/2005 | Oyama et al. | 210/490 |
| 2004/0018609 A1 | 1/2004 | Maekawa | |

FOREIGN PATENT DOCUMENTS

| | | |
|---|---|---|
| EP | 881287 | 12/1998 |
| JP | 2-286093 | 11/1990 |
| JP | 4-4892 | 1/1992 |
| JP | 4-23979 | 1/1992 |
| JP | 6-169783 | 6/1994 |

* cited by examiner

*Primary Examiner*—Herbert J. Lilling
(74) *Attorney, Agent, or Firm*—Wenderoth, Lind & Ponack, L.L.P.

(57) ABSTRACT

Mesophilic methane bacteria obtained from digested sludge are acclimatized in an $H_2/CO_2$ medium and the acclimatized methane bacteria are grown on a support inclusive of inorganic nutritional salts of trace metal elements by using an immobilized bed bioreactor. The grown bacteria are allowed to metabolize a mixed gas, prepared by adding hydrogen to at least one of coal gas and biogas, into methane and at the same time, cobalamin contained in the fermented liquor is recovered as an extracellular product in the form of cyanocobalamin by using potassium cyanide to thereby produce vitamin $B_{12}$ efficiently in a high content and high yield.

2 Claims, 6 Drawing Sheets

FIG. 6  RELATIONSHIP BETWEEN METHANE BACTERIA ACTIVITY IN IMMOBILIZED BED FERMENTATION TANK AND VITAMIN $B_{12}$ CONTENT

METHOD FOR PRODUCING VITAMIN B12 FROM HYDROGEN-METABOLIZING METHANE BACTERIUM

This application is a divisional application of Ser. No. 10/182,624, filed Nov. 25, 2002 now U.S. Pat. No. 6,972,188, which is a 371 application of PCT/JP01/00720, filed Feb. 1, 2001.

FIELD OF THE INVENTION

The invention of this application relates to the method for producing vitamin $B_{12}$.

It has been known that cobalamin, that is, vitamin $B_{12}$ analogues can be chemically synthesized with difficulty and biosynthesized from bacteria or actinomycetes, and yeast, fungi, plants and animals have no ability to biosynthesizing vitamin $B_{12}$. A method of extracting vitamin $B_{12}$ from cell bodies of propionibacteria using methanol as a substrate is being put to industrial use. Although such vitamin $B_{12}$ is primarily utilized as drugs, there are increased demands for the development of functional foods and for health-maintaining foods to which vitamin $B_{12}$ is added. And therefore a development of less the cost vitamin $B_{12}$ is desired in recent years.

BACKGROUND ART

Heretofore, in the production of vitamin $B_{12}$ from propionibacteria, methanol is used as a substrate and the growth of these bacteria is very slow because these bacteria are facultative anaerobe. Also, because propionic acid is transformed into acetic acid, and the acetic acid caused growth inhibition. So that the density of cell bodies in fermented liquor is not increased and the amount of vitamin $B_{12}$ that can be extracted from the cell body is the order of 1 mg/L, showing that the conventional process has low productivity. And Shiro Nagahisa et al. (Seibutsu-kogaku Kaishi, 76(6), 447–455, 1998) used an immobilized bed bioreactor of methane bacteria wherein methanol is used as a substrate to compare the yield of vitamin $B_{12}$ of methane bacteria with that of propionibacteria and obtained vitamin $B_{12}$ from methane bacteria in a yield 10 times higher than that obtained from propionibacteria. However, the resulting solution contains, as its major component, collinoid having small cobalamin types. In this case, there is the problem that the recovery of vitamin $B_{12}$ is not improved because a process of separation from methanol is complicated and this method does not bring about a reduction in production cost since the content of vitamin $B_{12}$ is small.

DISCLOSURE OF THE INVENTION

In view of this situation, it is an object of the invention of this application solves the prior art problems as aforementioned and to provide a new method ensuring that vitamin $B_{12}$ can be efficiently produced in a high content and high yield.

BRIEF DESCRIPTION OF THE DRAWINGS

It is to be noted that the symbols in FIG. 4 and FIG. 5 represent the following parts.
1. Porous ceramics
2. Reactor
3. Support packed vessel
4. Negative electrode
5. Diffusing nozzle
6. Electromagnetic valve
7. Gas holder
8. Biogas or coal gas feed pipe
9. Oxygen discharge section
10. Positive electrode
11. Electromagnetic valve
12. Electromagnetic valve
13. Pressure detection controller
14. Check valve
15. Drain valve
16. Drain valve
17. Electrolysis apparatus
18. Ultra-filtration membrane unit
19. Pressure control electromagnetic valve
20. Gas density detection controller
21. Liquid supply nozzle for a medium

BEST MODE FOR CARRYING OUT THE INVENTION

The invention of this application of this case has been made to solve the aforementioned problem and, first, provides a method for producing vitamin $B_{12}$, the method comprising acclimatizing mesophilic methane bacteria obtained from digested sludge in a $H_2/CO_2$ medium, growing the acclimatized methane bacteria on a support inclusive of inorganic nutritional salts of trace metal elements by using an immobilized bed bioreactor, allowing the bacteria to metabolize a mixed gas, prepared by adding hydrogen to at least one of coal gas and biogas, into methane and, at the same time, recovering cobalamin contained in the fermented liquor as an extracellular product in the form of cyanocobalamin by using potassium cyanide.

Second, the invention of this application provides a method for producing vitamin $B_{12}$, the method comprising acclimatizing mesophilic methane bacteria obtained from digested sludge in a $H_2/CO_2$ medium, growing the acclimatized methane bacteria in a suspension culture reactor combined with a ultra-filtration membrane and containing trace metal elements, recovering extracellular cobalamin contained in the solution penetrated through the ultra-filtration membrane as cyanocobalamin by using potassium cyanide and allowing the methane bacteria to return to the culture solution from the ultra-filtration membrane and culturing the methane bacteria to metabolize a mixed gas prepared by adding hydrogen to at least one of coal gas and biogas.

Also, the invention of the patent application of this case provides, third, in the above method, a method in which the concentration of the trace metals is made to be 10 to 1000 times higher than that of the standard composition and, fourth, a method in which the ratio of Co/Fe among the concentrations of the trace metal salts in the medium of hydrogen-metabolizing methane bacteria is made to be 10 to 100 times higher than the standard composition ratio.

Further, the invention provides, fifth, a method for fermenting methane as the method of adding hydrogen to coal gas and biogas, the method comprising placing a negative electrode portion at the upper position and a positive electrode portion at the lower position through a porous ceramics on the bottom of an immobilized bed or suspension type bioreactor, applying D.C. voltage to electrolyze water in a culture solution thereby generating hydrogen, which is utilized in a trace element-enriched support immobilized bed or complex type methane fermenting bioreactor, and emitting oxygen into the atmosphere and, sixth, a method of reforming gas, the method comprising applying D.C. voltage to the residue obtained by extracting cobalamin, which is an extracellular product, as cyanocobalamin by using potassium cyanide to perform electrolysis and supplying hydrogen obtained by the above extraction to coal gas and biogas containing carbon monoxide and carbon dioxide to perform methanation by using a membrane-combined bioreactor or an immobilized bed reactor.

The invention of this application has been completed taking the opportunity of acquiring the following findings and also based on these findings. Specifically, the inventors of the patent application of this case have found that in an experiment made to try converting $CO_2$ (about 40%) in biogas into $CH_4$ (methanation) by adding $H_2$ in the development of a support inclusive of trace elements/inorganic nutrient salts (JP-A9-140181 and JP-A-10-327850), it is clarified from the calculation of the material balance of vitamin $B_{12}$ that extracellular dilution of vitamin $B_{12}$ present in a culture solution is caused and vitamin $B_{12}$ existing in a cell body is only 30% when the amount of vitamin $B_{12}$ is 70% of the total amount in the experiment of methanation ($4H_2+CO_2 \rightarrow CH_4+2H_2O$), although it is said in the conventional reports that a large part of vitamin $B_{12}$ exists in a cell body in the case of using bacteria other than methane-generating bacteria and the methane bacteria obtained by selectively culturing mesophilic methane bacteria by acclimatizing culture using, as a substrate, a mixed gas of hydrogen and carbon dioxide is capable of extracting highly concentrated cobalamin (analogues of vitamin $B_{12}$) as cyanocobalamin from the fermented liquor.

Firstly, in the method of the invention of the patent application of this case, basically;

1) mesophilic methane bacteria obtained from digested sludge are acclimatized in a $H_2/CO_2$ medium;

2) the acclimatized methane bacteria are grown using an immobilized bed bioreactor on a support inclusive of inorganic nutrient salts of trace metal elements;

3) a mixed gas prepared by adding hydrogen to coal gas and biogas is metabolized into methane and at the same time;

4) cobalamin present in the fermented liquor as an extracellular product as cyanocobalamin, namely, vitamin $B_{12}$ by using potassium cyanide.

In this method, for example, it is effective to raise the concentration of the trace metals 10 to 1000 times higher than that used conventionally in the above inclusive support.

In, for example, suspension culture in a membrane-combined type bioreactor equipped with an ultra-filtration membrane, it is effective to raise each concentration of the trace metal salts and nutrient salts 10 to 1000 times higher than that used conventionally. As to this ultra-filtration membrane-combined suspension culture, in this invention, the aforementioned method for producing vitamin $B_{12}$ is provided resultantly, wherein mesophilic methane bacteria obtained from digested-sludge are acclimatized in a $H_2/CO_2$ medium, the acclimatized methane bacteria are grown in the ultra-filtration membrane-combined suspension culture reactor containing trace metal elements, extracellular cobalamin contained in the solution penetrated through the ultra-filtration membrane is recovered as cyanocobalamin by using potassium cyanide and the methane bacteria are allowed to return to the culture solution from the ultrafiltration membrane and cultured to metabolize a mixed gas prepared by adding hydrogen to at least one of coal gas and biogas.

In all of the aforementioned methods in the present invention, the concentration of cobalamin in the culture salts can be increased by such a partial alteration of a medium that particularly the ratio of Co/Fe is 10 to 100 times higher. Therefore, the invention reforms coal gas and biogas which are obtained by methanation for converting 100% of coal gas and biogas containing a large amount of $CO_2$ and CO into $CH_4$, and at the same time, cobalamin is converted into cyanocobalamin (vitamin $B_{12}$) by using potassium cyanide, which is recovered from the culture solution. The recovery of vitamin $B_{12}$ is very simplified as compared with a conventional method of the recovery from cell bodies and the concentration of vitamin $B_{12}$ is 50 to 100 times higher than that obtained using propionibacteria. Also the recovery from this culture medium reaches 2 to 10 times that from methanol-metabolizing methane bacteria (Shiro Nagai et al. 1996, Seibutsu-kogaku Kaishi, 74(6), 447–455), resulting in that the production cost of vitamin $B_{12}$ can be remarkable reduced.

Next, the invention of this application will be further explained according to the drawings attached.

Figure 1:
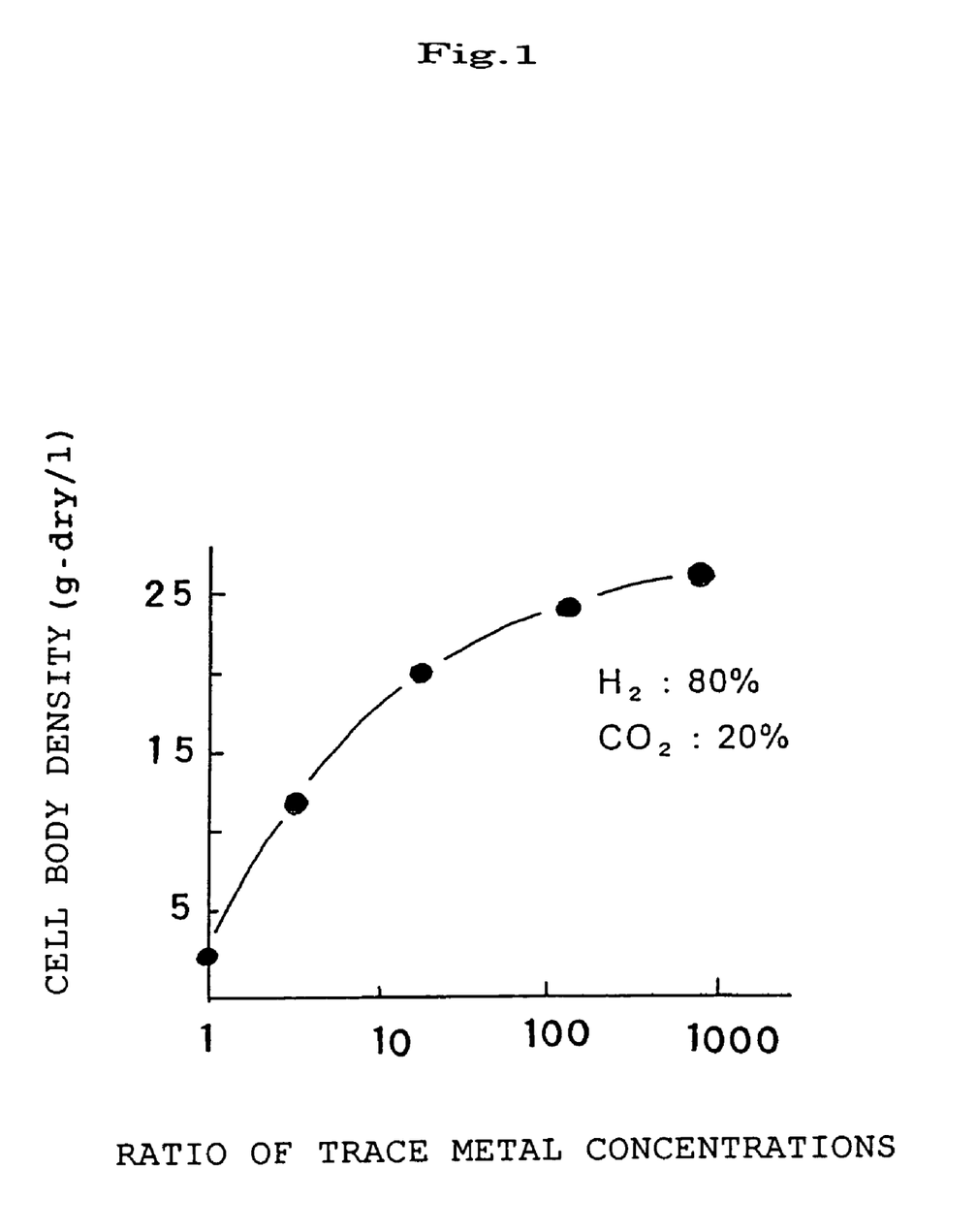
FIG. 1 shows a view illustrating an increase in the density of methane bacteria.

FIG. 1 is a view showing an increase in the density of cell bodies of methane bacteria when, using a gas containing 80% of hydrogen and 20% of carbon dioxide as the substrate, methane bacteria which are sufficiently acclimatized using a liquid type standard synthetic medium are continuously cultured at the same medium temperature (35° C. to 36° C.) using a support inclusive of inorganic nutrient salts in which each concentration of the nutrient salts and trace metal salts is raised 10 to 1000 times higher than that used in conventional methods (JP-A-9-140181 and JP-A-10-327850, trace elements/inorganic nutrient salts diffusion type cell body culture support). When the density of cell bodies of methane bacteria was 26 g-dry/L, the concentration of vitamin $B_{12}$ reached 185 mg/L. This concentration was 50 to 100 times that obtained in the case of using propionibacteria.

Figure 2:
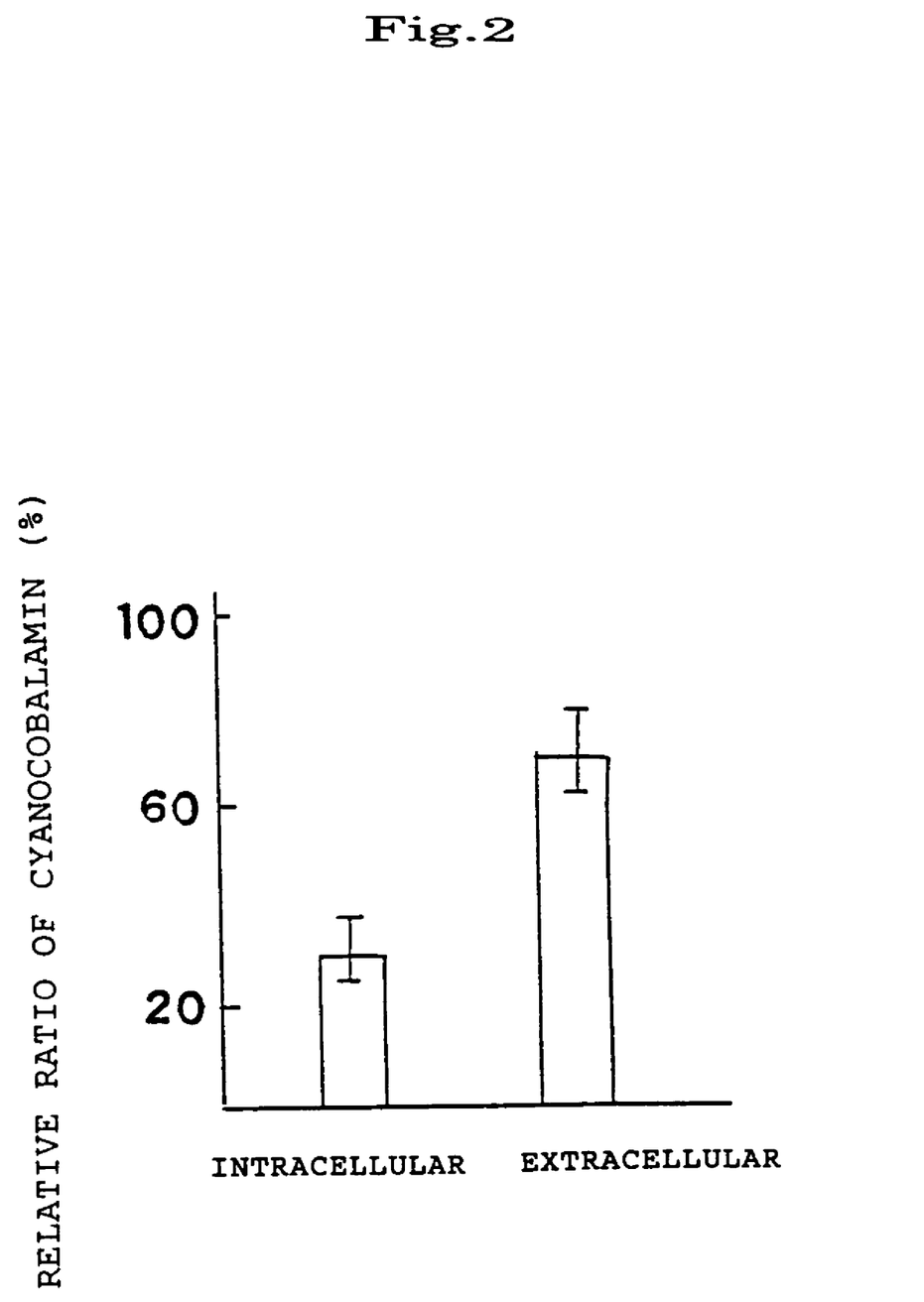
FIG. 2 shows a view illustrating the ratio of extracellular vitamin $B_{12}$ to intracellular vitamin $B_{12}$.

Also, in FIG. 2, 80% of hydrogen and 20% of carbon dioxide were blown as a substrate into a synthetic medium having a trace metal concentration 10 times higher than that of a conventional method to examine the ratio of intracellular vitamin $B_{12}$ to extracellular vitamin $B_{12}$ in the suspension culture solution to find that each proportion was 30% and 70%. So it is considered that the separation of vitamin $B_{12}$ eluted extracellularly by using a support inclusive of trace elements/nutrient salts rather enables efficient production.

Figure 3:
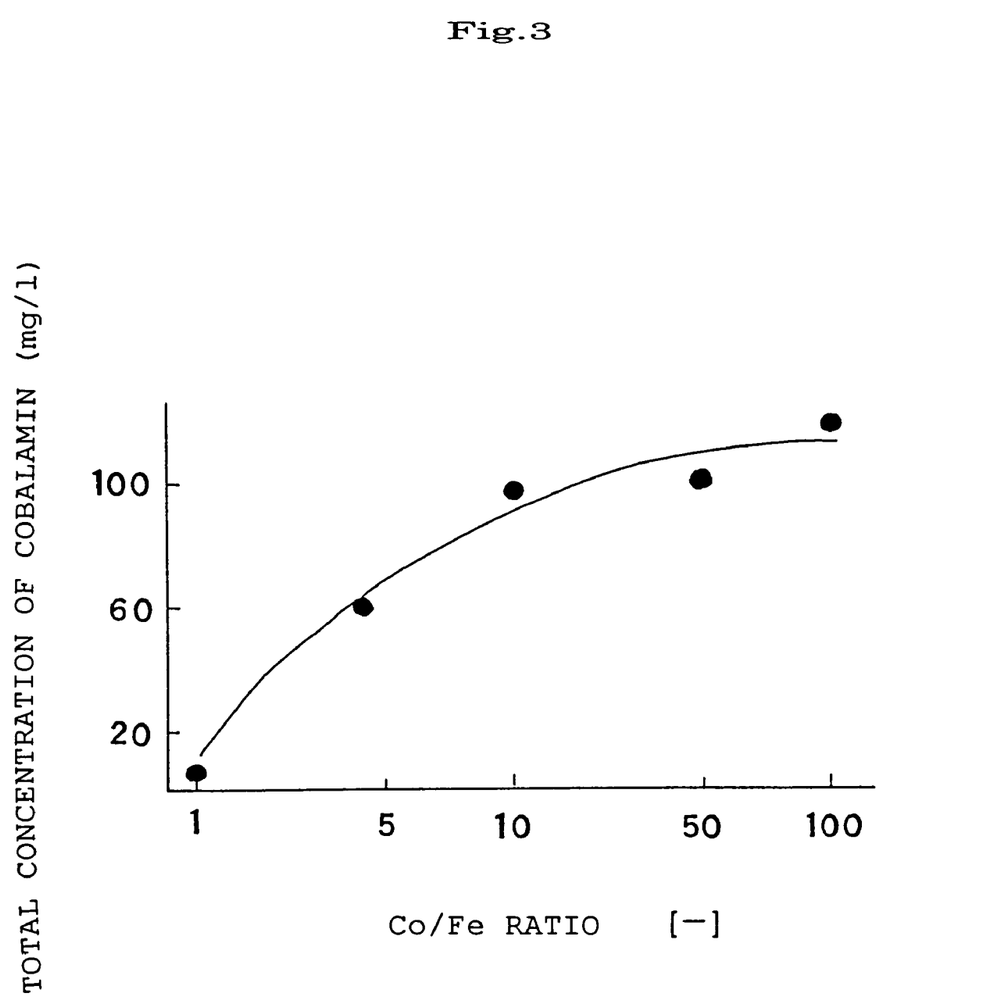
FIG. 3 shows a view illustrating the relation between Co/Fe ratio and the density of cyanocobalamin.

Then, FIG. 3 shows the density of cyanocobalamin when operating a bioreactor using, as parameters, the ratio of cobalt to iron which are the trace elements in the support inclusive of the trace elements/nutrient salts by using, as the substrate, a mixed gas having a carbon dioxide concentration of 40% to 60% and a hydrogen concentration of 60%. Cobalamin is an analogue of vitamin $B_{12}$ and it is understood that cobalamin strongly requires cobalt.

Figure 4:
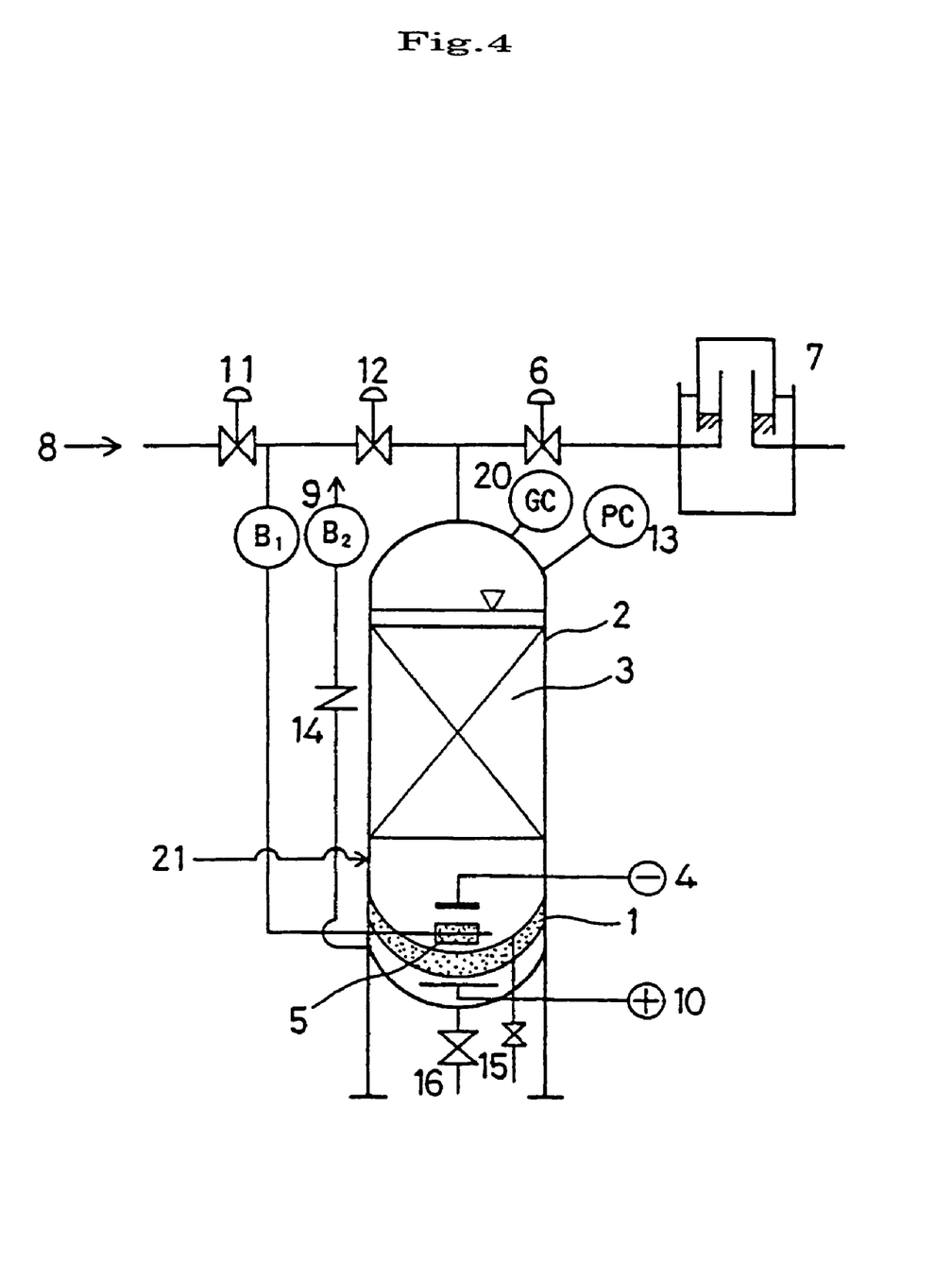
FIG. 4 shows an example of the structure of a bioreactor.

In FIG. 4, as a method of adding hydrogen to carbon dioxide gas and biogas, a porous ceramics 1 is placed on the bottom of a reactor 2 in a biogas reactor, a metal electrode (titanium and iron) corresponding to a positive electrode 10 is placed under the porous ceramics 1 in a solution at the lower most portion of the reactor, an electrode plate of a negative electrode 4 made of platinum or titanium is placed just above a diffusing nozzle 5 disposed just above the porous ceramics 1 and a voltage of 20 to 100 V is applied. Hydrogen is thereby generated on the plate of the negative electrode 4. Although oxygen is generated on the electrode plate of the positive electrode 10, it is diffused into air by means of a blower B2 by disposing an oxygen-emitting section 9. If the size of the clearance of the porous ceramics 1 is designed to be as small as 1/20 to 1/100 of the diameter of the generated oxygen cell and the pressure is always kept higher than the atmospheric pressure by using a blower, oxygen generated by electrolysis never penetrates into the reactor 2 through the porous ceramics 1 and an absolutely anaerobic condition in the bioreactor can be kept. A support packed vessel 3 is incorporated into the reactor 2 such that a support inclusive of trace elements is disposed as an immobilized bed. The volume of the support packed vessel is designed to be 30 to 60% of the effective volume to fill it. Coal gas and biogas are introduced from a biogas or coal gas feed pipe 8 according to the indication of a pressure detection controller 13. These gases are circulated by the operation of a blower B1 and by an open-operation of electromagnetic valves 11 and 12. When the concentration of carbon dioxide is decreased and the concentration of $CH_4$ is increased, an electromagnetic valve 6 is opened according to the indication of a gas temperature detection controller designated as the symbol 20 to feed methane to a gasholder 7. When the pressure in the bioreactor 2 is dropped, the electromagnetic valves 6 and 12 are opened to supply gas newly from the biogas or coal gas feed pipe 8.

Figure 5:
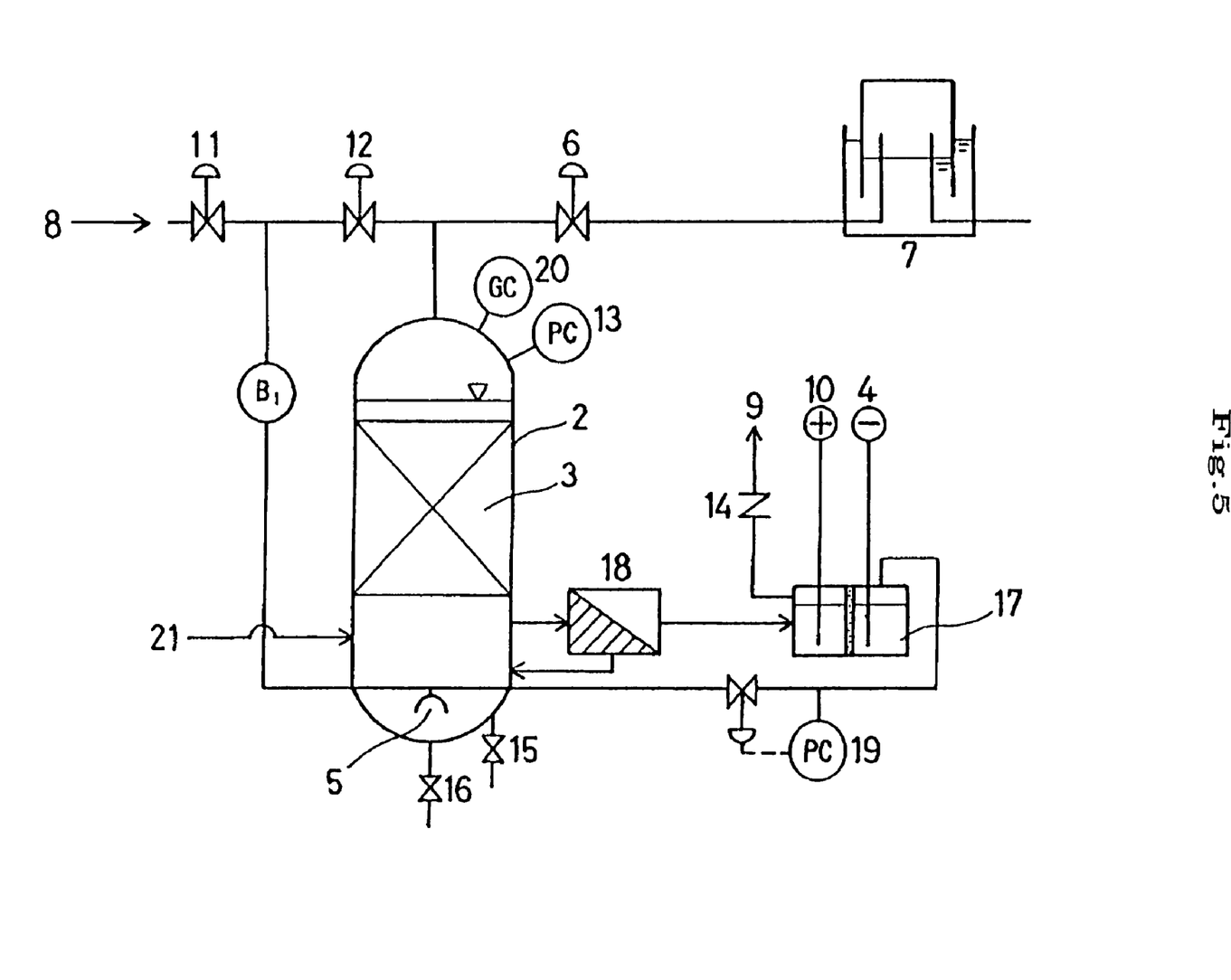
FIG. 5 shows another example of the structure of a bioreactor.

In FIG. 5, the fermented liquor containing cobalamin is decomposed in an electrolysis apparatus 17 and only hydrogen is supplied to the bioreactor 2. Methane bacteria living in the immobilized bed of the support packed vessel 3 run methanation to convert carbon dioxide, fed from the biogas or coal gas feed pipe 8, into methane by hydrogen supplied from the electrolysis apparatus 17. When the concentration of methane in the bioreactor rises and reaches close to 100%, the valve 6 is opened by the gas detection controller 20 to feed methane to the gasholder 7. When the pressure in the bioreactor is dropped, the electromagnetic valves 6 and 12 are put into a state of closed-operation and gas is newly supplied from the biogas or coal gas feed pipe 8 by an open-peration of the electromagnetic valve 11. In this manner, both FIG. 4 and FIG. 5 show a semi-continuous operation when gas is used as a substrate. On the other hand, because the concentration of cobalamin rises in the liquor, the concentration is always inspected and the liquor is withdrawn in a fixed amount by the operation of drain valves designated as the symbols 15 and 16 respectively when the concentration reaches a maximum to recover vitamin $B_{12}$ from this liquor. As to the withdrawal of the liquor, it is withdrawn using the drain valve 15 or 16 on the premise that new gas is supplied, provided that these operational procedures are carried out so as to prevent the intrusion of oxygen into the bioreactor 2. Thereafter, a medium solution is supplied from a medium solution supply nozzle 21 as shown in FIG. 4 and FIG. 5 by using a pump.

These methods and apparatuses illustrated in FIG. 4 and FIG. 5 are useful in the practice of any one of the first to fourth methods of this invention.

Next, examples of this invention will be explained.

EXAMPLES

<1> In an experiment using batch suspension culture wherein the concentration of cobalt chloride among the concentration of trace elements which concentration was 10 times higher than that of conventional method was raised, the concentration of vitamin $B_{12}$ in the culture solution was 25.2 mg/L after 48 hours in the case of using, as a substrate, a synthetic gas containing 20% of $CO_2$ and 80% of $H_2$. The conventional bibliographic value of the concentration of vitamin $B_{12}$ obtained from propionibacteria was 0.5 to 1 mg/L. It was therefore confirmed that the method of this invention had high yield and cyanocobalamin eluted extracellularly so that it was recovered with ease.

<2> A solution having a concentration 1000 times higher than that of a conventional method was confined in a support inclusive of a trace element/nutrient fixed to the support and then the support was packed in an immobilized bed bioreactor having a volume of 5 L. Hydrogen generated by a hydrolysis process in a culture solution was continuously supplied to biogas consisting of 40% of $CO_2$ and 60% of $CH_4$ to carry out a continuous operation for reforming the biogas, whereby 98 to 99% of the biogas could be converted into $CH_4$. Also, at the same time, the concentration of vitamin $B_{12}$ in the culture solution reached 180 mg/L. This concentration was 50 to 100 times that obtained using propionibacteria and the production rate was also 25 to 50 times that obtained using propionibacteria.

From the above, the specific action and marked results of the examples are summarized as follows:

1. Vitamin $B_{12}$ is recovered from a culture solution having enriched trace metal salts but not from a cell body itself. Therefore, cell bodies can be kept in a high density and cobalamin, which is an extracellular product, can be recovered in by far much amount as compared with the case of using a conventional method and the yield of vitamin $B_{12}$ can be raised.

2. Hydrogen can be supplied from a solution itself contained in the bioreactor by an electrolysis process. This makes it possible to reform biogas and coal gas and to attain high energization of these gases.

3. In the method of recovering vitamin $B_{12}$, the uses of potassium cyanide simplify the recovery of vitamin $B_{12}$ as cyanocobalamin, decreasing the production cost of vitamin $B_{12}$ more greatly.

Figure 6:
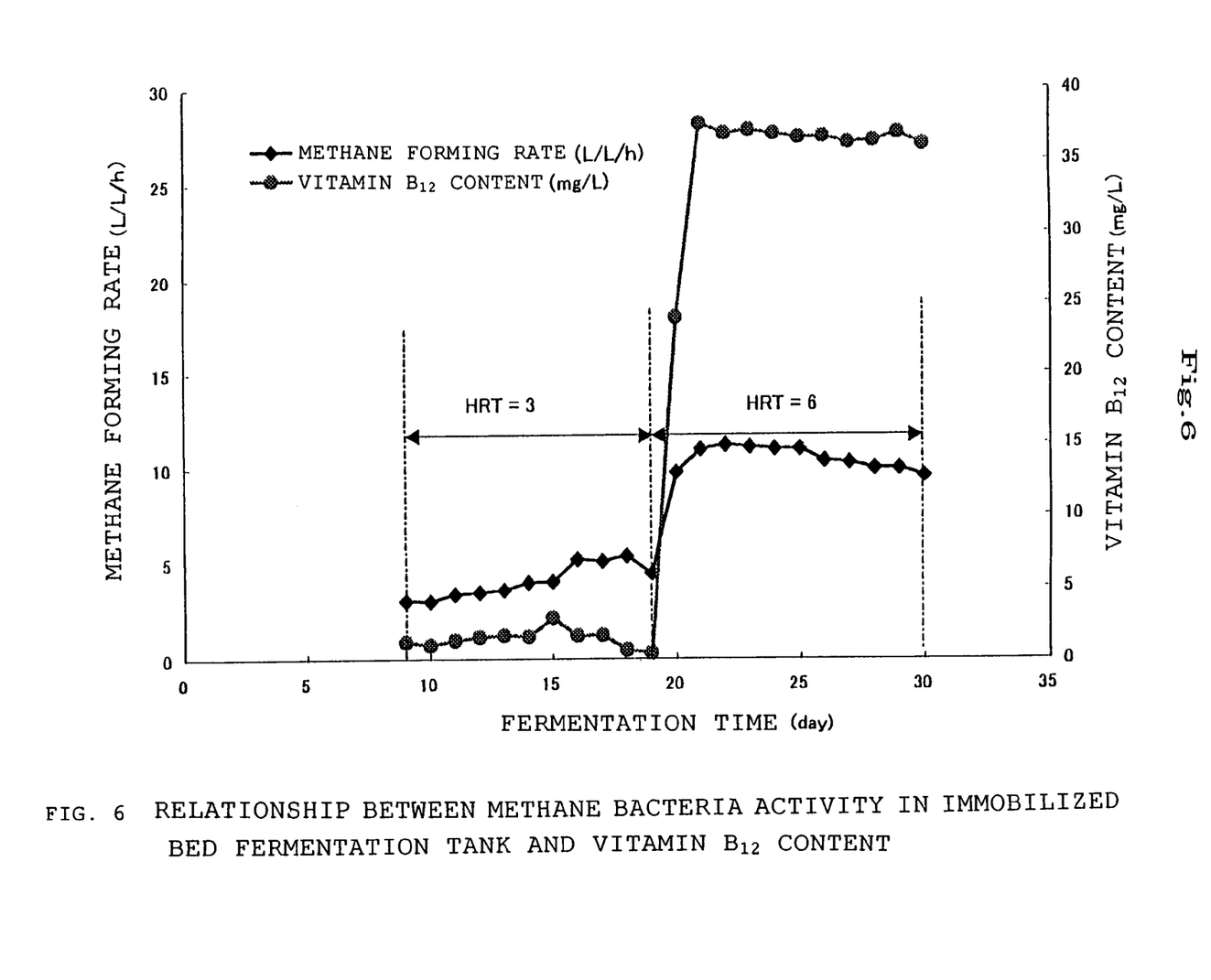
FIG. 6 shows a view illustrating the relation between the activity of methane bacteria and the content of vitamin $B_{12}$ in an immobilized bed fermentor.

<3> A solution having a trace element concentration 1000 times higher than that of a conventional method was confined in a support inclusive of nutrient salts and then the support was packed in an immobilized bed bioreactor having a volume of 5 L. A continuous sulfurization experiment was conducted in a medium having a concentration 100 times higher than that of a conventional method in two conditions of mean residence time (HRT) of 3 days and 6 days. At this time, hydrogen generated by electrolyzing a supernatant liquor side medium was continuously supplied to biogas consisting of 40% of $CO_2$ and 60% of $CH_4$ to carry out a continuous operation for reforming the biogas for 30 days. The results are shown in FIG. 6. First 9 days corresponds to 3 times the HRT required for start-up. Considering that the system is in an unsteady state during this period, the production rate of methane and cyanocobalamin vitamin $B_{12}$ (perfect type) were measured since 9th day till 30th day. As a result, in the case where HRT was 6 days, the perfect type vitamin $B_{12}$ was kept in a concentration of about 37.5 mg/L and the production rate of methane was 11.5 L/L/h. When the rate of the production of the perfect type vitamin $B_{12}$ is compared taking HRT into account, it is 110 to 160 times that of the production from propionibacteria. As compared with the results of TAPPAN et al. (1987: Applied Microbiology and Biotechnology, 26: 511–516), the results of FIG. 6 show that a twenty-fold increase in the production rate of the perfect type vitamin $B_{12}$ is attained.

Also, the density of methane bacteria in the experiment shown in FIG. 6 reaches 40 g/L. It is therefore clarified that the perfect type vitamin $B_{12}$ is eluted in a large amount from methane bacteria, offering possibilities of stabilizing the industrial production of vitamin $B_{12}$ and of achieving low production cost.

INDUSTRIAL APPLICABILITY

As mentioned above in detail, the invention of ensures that vitamin $B_{12}$ can be produced in a high content and high yield by far more efficiently than in the case of conventional production.

What is claimed is:

1. A method for fermenting methane, the method comprising placing a negative electrode portion at the upper position and a positive electrode portion at the lower position through a porous ceramics on the bottom of an immobilized bed or suspension type bioreactor, applying D.C. voltage to electrolyze water in a culture solution thereby generating hydrogen, which is utilized in a trace element-enriched support immobilized bed or a membrane combined type methane fermenting bioreactor, and emitting oxygen into the atmosphere.

2. A method of reforming gas, the method comprising applying D.C. voltage to the residue obtained by extracting cobalamin, which is an extracellular product, as cyanocobalamin by using potassium cyanide to perform electrolysis and supplying hydrogen obtained by the extraction to coal gas and biogas containing carbon monoxide and carbon dioxide to perform methanation by using a membrane-combined bioreactor or an immobilized bed reactor.

* * * * *